United States Patent [19]

Nickisch et al.

[11] Patent Number: 4,542,024

[45] Date of Patent: Sep. 17, 1985

[54] 15,16-METHYLENE-17α-PREGNA-4,6-DIENE-21-CARBOXYLIC ACID SALTS, PHARMACEUTICAL PREPARATIONS CONTAINING THEM AND A PROCESS FOR THEIR PRODUCTION

[75] Inventors: Klaus Nickisch; Dieter Bittler; Henry Laurent; Rudolf Wiechert; Wolfgang Losert, all of Berlin, Fed. Rep. of Germany

[73] Assignee: Schering Aktiengesellschaft, Berlin, Fed. Rep. of Germany

[21] Appl. No.: 630,552

[22] Filed: Jul. 13, 1984

[30] Foreign Application Priority Data

Jul. 15, 1983 [DE] Fed. Rep. of Germany ....... 3326013

[51] Int. Cl.$^4$ .......................... C07J 9/00; A61K 31/56
[52] U.S. Cl. .................. 514/178; 260/397.1; 260/239.57
[58] Field of Search .............. 260/397.1, 239.57; 424/238

[56] References Cited

U.S. PATENT DOCUMENTS 4,150,127 4/1979 Anner et al. .................. 260/239.57
4,291,029 9/1981 Wiechert et al. ............. 260/239.57
4,450,107 5/1984 Nickisch et al. ............. 260/239.57

OTHER PUBLICATIONS

European Search Report.

Primary Examiner—Elbert L. Roberts
Attorney, Agent, or Firm—Millen & White

[57] ABSTRACT

New 15,16-methylene-17α-pregna-4,6-diene-21-carboxylic acid salts of formula I

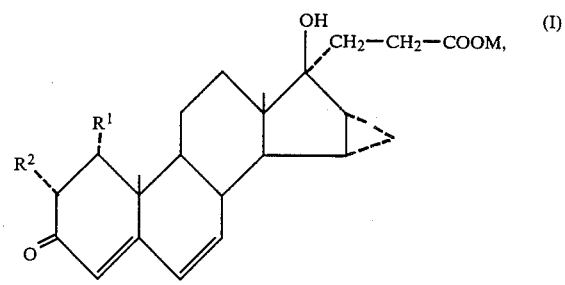

wherein
  $R^1$ and $R^2$ each alone is hydrogen or together they form an additional CC bond or a methylene group,
  M is an alkali metal,
and the methylene group in the 15,16 position is in the α or β position, in addition to having a strong antialdosterone effect, have reduced antiandrogenic and progestogenic side effects.

15 Claims, No Drawings

15,16-METHYLENE-17α-PREGNA-4,6-DIENE-21-CARBOXYLIC ACID SALTS, PHARMACEUTICAL PREPARATIONS CONTAINING THEM AND A PROCESS FOR THEIR PRODUCTION

BACKGROUND OF THE INVENTION

This invention relates to 15,16-methylene-17α-pregna-4,6-diene-21-carboxylic acid salts, pharmaceutical preparations containing them and a process for producing them.

SUMMARY OF THE INVENTION

It is an object of this invention to provide new compounds having valuable pharmacological properties.

Upon further study of the specification and appended claims, further objects and advantages of this invention will become apparent to those skilled in the art.

These objects have been attained by providing 15,16-methylene-17α-pregna-4,6-diene-21-carboxylic acid salts of formula I

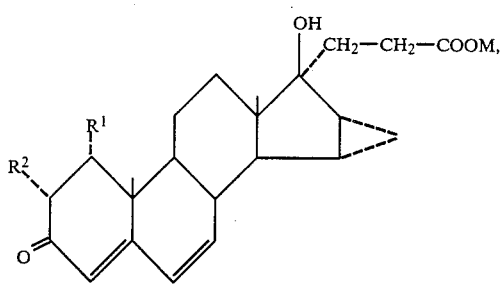

wherein
$R^1$ and $R^2$ each alone is hydrogen or together they form an additional CC bond or a methylene group, and
M is an alkali metal
and the methylene group in the 15,16 position is in the α or β position.

DETAILED DISCUSSION

The new compounds of formula I are alkali salts of 3-substituted propionic acid. Suitable salts include those of potassium, sodium or lithium, preferably potassium.

The new compounds of formula I have the property of cancelling or reversing the effect of aldosterone or desoxycorticosterone on sodium and potassium salt elimination. The new compounds are readily water-soluble, e.g., as the known potassium canrenoate, but they are superior to potassium canrenoate in antialdosterone effect and have a reduced antiandrogenic and progestogenic side effect. The antialdosterone effect was measured in the conventional Hollmann test model (Naunyn-schmiedebergs Arch. Exp. Path. Pharmak. 247 (1964) page 419).

The relative values of the antialdosterone potency (with potassium canrenoate=1) of compounds A, B and C according to this invention are summarized in the following table.

A. 17β-hydroxy-15β, 16β-methylene-3-oxo-17α-pregna-1,4,6-triene-21-carboxylic acid potassium salt, B. 1α, 2α; 15β, 16β-dimethylene-17β-hydroxy-3-oxo-17α-pregna-4,6-diene-21 carboxylic acid potassium salt, and C. 17β-hydroxy-15α, 16α-methylene-3-oxo-17α-prena-4,6-diene-21-carboxylic acid potassium salt.

TABLE

| Compound | Relative Antialdosterone Effect |
|---|---|
| D canrenoate | 1 |
| A | 2–3 |
| B | 1–2 |
| C | 1–2 |

The new compounds are suitable for treating conditions, e.g., in mammals, including humans, in which a primary or secondary hyperaldosteronism is involved. These conditions include, for example, cirrhosis of the liver with ascites and edemas, serious cardiac insufficiency, nephrotic syndrome, traumatic cerebral edema, etc.

The active ingredients are preferably administered intravenously in aqueous solution. The dosage of the active ingredients can be conventionally varied from case to case and depends on the type and severity of the condition. In general, the amount of active ingredient administered to humans will be about 50 to 600 mg per day. The aqueous solution of the active ingredient can typically be formulated in ampoules which contain 50 to 200 mg of the drug. In general, administration of the compounds of this invention for the applicable indications will be analogous to that of the known agent, potassium canrenoate.

The pharmacologically active compounds of this invention can be processed in accordance with conventional methods of galenic pharmacy to produce medicinal agents for administration to patients, e.g., mammals, including humans. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparation can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Suitable dosages for a given host can be determined using conventional considerations, e.g., by customary comparison of the differential activities of the subject compound and of a known agent, e.g., by means of an appropriate, conventional pharmacological protocol.

Production of the compounds of formula I, according to this invention, can be accomplished according to methods known in the art, e.g., from the corresponding 21,17-carbolactones of formula II

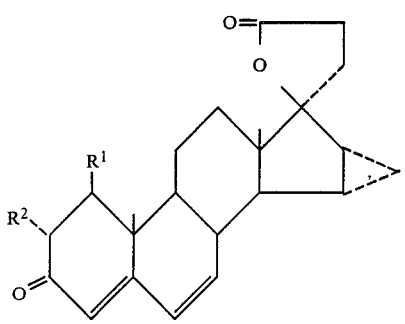

wherein
$R^1$ and $R^2$ are as defined above,
by opening the lactone ring by action of an alkali.

For this purpose, the carbolactone can be heated to about 50°–100° C. with an equimolar amount of alkali metal hydroxide in a lower alcohol such as, for example, methyl alcohol, ethyl alcohol, isopropyl alcohol, propyl alcohol or butyl alcohol. Sodium, potassium or lithium hydroxide is suitable as the alkali hydroxide.

The 21,17-carbolactones of general formula II used as starting materials, are known, for example, from DE-OS 27 22 706, whose disclosure is incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

9 ml of a 1N potassium hydroxide solution in methyl alcohol is added to a solution of 3.0 g of 15β, 16β-methylene-3-oxo-17α-pregna-1,4,6-triene-21, 17-carbolactone in 45 ml of isopropyl alcohol and refluxed for 30 minutes. After cooling, the reaction mixture is added to 45 ml of ice-cold diethyl ether, the precipitate is filtered off and rewashed with diethyl ether. The resulting precipitate is then absorptively precipitated with ethyl acetate, suctioned off and dried in a vacuum. 2.6 g of 17β-hydroxy-15β, 16β-methylene-3-oxo-17α-pregna-1,4,6-triene-21-carboxylic acid potassium salt is obtained.

IR (KBr): 3410, 1650, 1600, 1580, 1400 cm$^{-1}$.

EXAMPLE 2

180 mg of 1α, 2α; 15β, 16β-dimethylene-17β-hydroxy-3-oxo-17α-pregna-4,6-diene-21-carboxylic acid potassium salt with a melting point of 183°–186° C. is obtained from 300 mg of 1α, 2α, 15β, 16β-dimethylene-3-oxo-17α-pregna-4,6-diene-21-17-carbolactone under the conditions described in Example 1.

IR (KBr): 3420, 1645, 1575, 1400 cm$^{-1}$.

EXAMPLE 3

620 mg of 17β-hydroxy-15β, 16β-methylene-3-oxo-17α-pregna-4,6-diene-21-carboxylic acid potassium salt is obtained from 1 g of 15β, 16β-methylene-3-oxo-17α-pregna-4,6-diene-21,17-carbolactone under the conditions described in Example 1.

IR (KBr): 3410, 1650, 1580, 1400 cm$^{-1}$.

EXAMPLE 4

325 mg of 17β-hydroxy-15α, 16α-methylene-3-oxo-17α-pregna-1,4,6-triene-21-carboxylic acid potassium salt is obtained from 500 mg of 15α, 16α-methylene-3-oxo-17α-pregna-1,4,6-triene-21,17-carbolactone under the conditions described in Example 1.

UV: $\epsilon_{283} = 22400$.

EXAMPLE 5

280 mg of 1α, 2α; 15α, 16α-dimethylene-17β-hydroxy-3-oxo-17α-pregna-4,6-diene-21-carboxylic acid potassium salt with a melting point of 281°–284° C. is obtained from 377 mg of 1α, 2α; 15α, 16α-dimethylene-3-oxo-17α-pregna-4,6-diene-21,17-carbolactone under the conditions described in Example 1.

UV: $\epsilon_{283} = 17900$.

EXAMPLE 6

180 mg of 17β-hydroxy-15α, 16α-methylene-3-oxo-17α-pregna-4,6-diene-21-carboxylic acid potassium salt with a melting point of 278°–283° C. is obtained from 350 mg of 15α, 16α-methylene-3-oxo-17α-pregna-4,6-diene-21,17-carbolactone under the conditions described in Example 1.

UV: $\epsilon_{283} = 24300$.

The preceding examples can be repeated with similar success by sutstituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

What is claimed is:

1. A 15,16-methylene-17α-pregna-4,6-diene-21-carboxylic acid salt of the formula

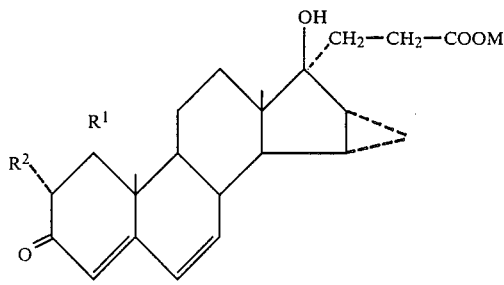

wherein
$R^1$ and $R^2$ each is hydrogen or together they form an additional CC bond or a methylene group,
M is an alkali metal, and the methylene group in the 15,16 position is in the α or β position.

2. A compound of claim 1, wherein the alkali metal is Na, K or Li.

3. A compound of claim 1, wherein the alkali metal is K.

4. A compound of claim 1, wherein $R^1$ and $R^2$ each is H.

5. A compound of claim 1, wherein $R^1$ and $R^2$ together form a CC bond.

6. A compound of claim 1, wherein $R^1$ and $R^2$ together form a methylene group.

7. 17β-hydroxy-15β, 16β-methylene-3-oxo-17α-pregna-1,4,6-triene-21-carboxylic acid potassium salt, a compound of claim 1.

8. 1α, 2α; 15β, 16β-dimethylene-17β-hydroxy-3-oxo-17α-pregna-4,6-diene-21-carboxylic acid potassium salt, a compound of claim 1.

9. 17β-hydroxy-15β, 16β-methylene-3-oxo-17α-pregna-4,6-diene-21-carboxylic acid potassium salt, a compound of claim 1.

10. 17β-hydroxy-15α, 16α-methylene-3-oxo-17α-pregna-1,4,6-triene-21-carboxylic acid potassium salt, a compound of claim 1.

11. 1α, 2α; 15α, 16α-dimethylene-17β-hydroxy-3-oxo-17α-pregna-4,6-diene-21-carboxylic acid potassium salt, a compound of claim 1.

12. 17β-hydroxy-15α, 16α-methylene-3-oxo-17α-pregna-4,6-diene-21-carboxylic acid potassium salt, a compound of claim 1.

13. A pharmaceutical composition comprising an effective amount of a compound of claim 1 and a pharmaceutically acceptable carrier.

14. A pharmaceutical composition of claim 13, wherein the amount of active agent is 50–200 mg.

15. A method of achieving an antialdosterone effect in a patient comprising administering an amount of a compound of claim 1 to the patient.

* * * * *